United States Patent
Hu et al.

(10) Patent No.: US 10,894,020 B2
(45) Date of Patent: Jan. 19, 2021

(54) HYBRID NANOPARTICLES CONTAINING BORON-DOPED GRAPHENE QUANTUM DOTS AND APPLICATIONS THEREOF

(71) Applicant: National Tsing Hua University, Hsinchu (TW)

(72) Inventors: Shang-Hsiu Hu, Hsinchu (TW); Yu-Lin Su, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 0 days.

(21) Appl. No.: 16/239,963

(22) Filed: Jan. 4, 2019

(65) Prior Publication Data

US 2020/0060983 A1 Feb. 27, 2020

(30) Foreign Application Priority Data

Aug. 23, 2018 (TW) .............................. 107129505 A

(51) Int. Cl.
| | |
|---|---|
| A61K 9/51 | (2006.01) |
| A61K 9/00 | (2006.01) |
| A61K 31/351 | (2006.01) |
| A61K 31/519 | (2006.01) |
| A61K 47/69 | (2017.01) |
| A61K 47/54 | (2017.01) |
| A61P 35/00 | (2006.01) |
| B82Y 40/00 | (2011.01) |
| B82Y 5/00 | (2011.01) |
| B82Y 30/00 | (2011.01) |

(52) U.S. Cl.
CPC .......... *A61K 9/5192* (2013.01); *A61K 9/0009* (2013.01); *A61K 9/513* (2013.01); *A61K 31/351* (2013.01); *A61K 31/519* (2013.01); *A61K 47/54* (2017.08); *A61K 47/6901* (2017.08); *A61P 35/00* (2018.01); *B82Y 5/00* (2013.01); *B82Y 30/00* (2013.01); *B82Y 40/00* (2013.01)

(58) Field of Classification Search
CPC .... A61K 9/5192; A61K 9/513; A61K 9/0009; A61K 31/351; A61K 31/519; A61K 47/6901; A61K 47/54; A61P 35/00; B82Y 40/00; B82Y 5/00; B82Y 30/00
See application file for complete search history.

(56) References Cited

PUBLICATIONS

Yang Liu, et al, Brain-Targeting Gene Delivery and Cellular Internalization Mechanisms for Modified Rabies Virus Glycoprotein RVG29 Nanoparticles, 30 Biomat. 4195 (Year: 2009).*
Shewaye Lakew Mekuria, et al, PAMAM Dendrimer Based Targeted Nano-carrier for Bio-imaging and Therapeutic Agents, 6 RSC Adv. 63761 (Year: 2016).*
Daniel Wu, et al, Phenylboronic acid-functionalized Polyamidoamine-Mediated Bcl-2 siRNA Delivery for Inhibiting the Cell Proliferation, 146 Coll. Surf. B: Biointerf. 318 (Year: 2016).*
Jin Zhou, et al, Carbon Dots Doped with Heteroatoms for Fluorescent Bioimaging: A Review, 184 Microchim Acta 343 (Year: 2017).*
Daniela Innazzo, et al, Graphene Quantum Dots for Cancer Targeted Drug Delivery, 518 Intl. J Pharmaceut. 185 (Year: 2017).*
Yu-Lin Su, et al, Rabies Virus Glycoprotein-Amplified Hierarchical Targeted Hybrids Capable of Magneto-Electric Penetration Delivery to Orthopic Brain Tumor, 321 J Control. Rel. 159 (Year: 2020).*
Stefan Wilhelm et al., "Analysis of nanoparticle delivery to tumours", Nature Reviews Materials vol. 1, Article No. 16014 (2016), Published Apr. 26, 2016, DOI https://doi.org/10.1038/natrevmats.2016.14.

* cited by examiner

*Primary Examiner* — Sean M Basquill
(74) *Attorney, Agent, or Firm* — WPAT, PC

(57) ABSTRACT

Provided is a hybrid nanoparticle, including an aggregate assembled from a plurality of polymeric molecules, and a plurality of boron-doped graphene quantum dots localized in the aggregate. The polymeric molecule is preferably a pH-responsive dendrimer; the polymeric molecule and the boron-doped graphene quantum dot may be separately associated with different drugs; and hybrid nanoparticle may further include a targeting molecule, such as a rabies virus glycoprotein. Also provided is a method of controlling disassembly of a hybrid nanoparticle, including applying a high-frequency magnetic field to the hybrid nanoparticle to induce disassembly thereof. Also provided is an application of the hybrid nanoparticle for preparing a tumor-penetrating drug carrier.

13 Claims, 8 Drawing Sheets
Specification includes a Sequence Listing.

```
SEQUENCE LISTING

<160> NUMBER OF SEQ ID NOS: 1

<210> SEQ ID NO 1
<211> LENGTH: 41
<212> TYPE: PRT
<213> ORGANISM: Artificial sequence
<220> FEATURE:
<223> OTHER INFORMATION: Rabies virus glycoprotein fragment

<400> SEQUENCE: 1

Tyr Thr Ile Trp Met Pro Glu Asn Pro Arg Pro Gly Thr Pro Cys Asp
1               5                   10                  15

Ile Phe Thr Asn Ser Arg Gly Lys Arg Ala Ser Asn Gly Gly Gly Gly
            20                  25                  30

Arg Arg Arg Arg Arg Arg Arg Arg Arg
        35                  40
```

HYBRID NANOPARTICLES CONTAINING BORON-DOPED GRAPHENE QUANTUM DOTS AND APPLICATIONS THEREOF

CROSS-REFERENCE TO RELATED APPLICATION

This application claims priority of Taiwan patent application No. 107129505, filed on Aug. 23, 2018, the content of which is incorporated herein in its entirety by reference.

BACKGROUND OF THE INVENTION

1. Field of the Invention

The present invention relates to a nanocarrier for drug delivery and application thereof. Particularly, the present invention relates to a hybrid nanoparticle containing boron-doped graphene quantum dots, and a method of controlling disassembly of the hybrid nanoparticle.

2. The Prior Art

For the purpose of diagnosing or treating diseases, academic researchers have extensively utilized nanocarriers as a platform for drug delivery in the body. In the field of cancer treatment, nanoscale delivery systems have been shown to enhance drug accumulation in tumors, thereby increasing drug efficacy on a cancerous area and reducing side effects on normal tissues. In addition, modification of nanocarriers with a targeting molecule that can be recognized by the target cells also facilitates the specific delivery of drugs to a particular tumor site.

However, in view of the statistics disclosed by Wilhelm et al. on the 2016 Nature-Review Materials, the average tumoral uptake of the therapeutic nanocarriers developed in the past decade was only about 0.7% of the injected dose, indicating that most of the nanocarriers are unable to effectively accumulate in the tumor area (S. Wilhelm, A. J. Tavares, Q. Dai, S. Ohta, J. Audet, H. F. Dvorak, W. C. W. Chan, *Nature Review Materials* 2016, 1, 16014). This observation may be attributed to the dense tumor-associated extracellular matrix and the high interstitial fluid pressure in tumors, both of which hinder the diffusion and constant retention of drugs in tumors. These characteristics of the tumor microenvironment also lead to the non-uniform drug distribution between the periphery and interior of the tumor, ultimately resulting in limited therapeutic effects. To solve this problem, scientists have attempted to inhibit the formation of extracellular matrix or to reduce the interstitial fluid pressure, but these strategies are under research.

There are other difficulties for chemotherapy of brain tumors, because the dense vascular endothelium that constitutes the blood-brain barrier (BBB) prevents most drugs from entering the brain, and only hydrophobic molecules with a molecular weight below 500 Da are able to pass the BBB. Therefore, the treatment of brain tumors mostly requires surgery combined with chemotherapy, but the survival rate is still low for brain tumor patients receiving such combined therapy. For example, the median survival of patients afflicted with glioblastoma multiforme (GBM) is only a dozen of months.

Currently, many types of nanocarriers are used in tumor treatment studies. One example is graphene, which is a material commonly used as drug carriers. Graphene is a two-dimensional carbon material with a network structure that is capable of adsorbing drugs through the surface 7E-7E interaction and being excited by light irradiation to fluoresce stably, and thus it is suitable for preparing drug carriers that are for both diagnosis and therapy. A graphene quantum dot (GQD), which is formed by reducing the size of graphene to nanometer scale, has lower cytotoxicity and better biocompatibility. It has been found by previous studies that graphene resonates under near-infrared light (usually with a wavelength of 808 nm) and leads to the photothermal conversion effect. Therefore, a method of combining a drug-loaded graphene with near-infrared irradiation has been used to kill tumor cells through therapeutic drugs and heat. In addition, studies have shown that visible light irradiation promotes the release of doxorubicin from the graphene carrier. However, conventional graphene or graphene quantum dots employing photolytic drug release can only be used to treat tumors close to the body surface rather than deep seated tumors or brain tumors due to the limited penetration of visible light into the body.

Accordingly, it is of necessity to develop a novel nanoformulation overcoming the aforementioned challenges encountered in tumor therapy.

SUMMARY OF THE INVENTION

As a result, the present invention provides a hybrid nanoparticle, including an aggregate assembled from a plurality of polymeric molecules, and a plurality of boron-doped graphene quantum dots (B-GQDs) localized in the aggregate.

In another aspect, the present invention provides a method of controlling disassembly of a hybrid nanoparticle, including the steps of obtaining the aforementioned hybrid nanoparticle, and applying a high-frequency magnetic field (HFMF) of 50 to 600 kHz to the hybrid nanoparticle to induce disassembly thereof.

In one further aspect, the present invention provides a method of preparing a tumor-penetrating drug carrier, including the step of incorporating a plurality of boron-doped graphene quantum dots in an aggregate assembled from a plurality of polymeric molecules to obtain the aforementioned hybrid nanoparticle, which is used as the tumor-penetrating drug carrier. In one embodiment, the tumor is a brain tumor.

In one embodiment of the present invention, the polymeric molecule is a stimuli-responsive polymeric molecule which allows the hybrid nanoparticle to change size in response to environmental alterations. One example is a pH-responsive dendrimer having a molecular weight of about 1,000 to 60,000 Da. Such dendrimer may further bind covalently or non-covalently a hydrophilic or hydrophobic drug through a hydrophilic or hydrophobic functional group. The drug may be an anti-tumor drug, for example, a cyclin-dependent kinases (CDKs) inhibitor such as palbociclib.

In another embodiment of the present invention, the boron-doped graphene quantum dot further binds to a hydrophobic drug, for example, an anti-tumor drug, including a nucleic acid (DNA) synthesis inhibitor such as erythromycin, an angiogenesis inhibitor, and a tumor metastasis inhibitor.

In still another embodiment of the present invention, the hybrid nanoparticle further includes a targeting molecule that directs the hybrid nanoparticle to a target tissue. For example, a rabies virus glycoprotein (RVG), which targets the nervous system, or a peptide fragment thereof is conjugated with the hybrid nanoparticle to direct it across the blood-brain barrier to a brain tumor.

In contrast to the size inconsistency and structural looseness that are often found in the conventional GQD-containing nanocomposites, which usually require strong acids for preparation and only encapsulate one specific drug, the hybrid nanoparticle of the present invention is easy to be prepared in large-scale within a short time and requires no need for strong acids. The hybrid nanoparticle of the present invention formed by self-assembly also possesses structural stability, thereby preventing the premature release of loaded drugs into non-target tissues after entry into the body and avoiding toxic side effects on normal tissues. In addition, the hybrid nanoparticle of the present invention can simultaneously carry drugs of different properties, such as hydrophilic drugs and hydrophobic drugs, because the polymeric molecules and B-GQDs are loaded with drugs separately.

The hybrid nanoparticle of the present invention may include stimuli-responsive polymeric molecules that are responsive to target tissue physiology. The term "stimuli-responsive" refers to the ability to change physical or chemical properties in response to environmental alterations in the target tissues, such as changing the state of aggregation in response to alterations in the environmental pH of the target tissues. When the hybrid nanoparticle contains pH-responsive polymeric molecules that form an aggregate of a larger size in a weakly acidic environment, the nanoparticle is more likely to retain in the tumor, thus increasing drug accumulation in the tumor.

It has been known in the art that controlled release of drugs from drug carriers at a specific site of the body not only improves the therapeutic effect on target tissues but also reduces toxic side effects on normal tissues. Distinct from the conventional methods for controlled drug release such as light-induced drug release, the present invention provides a new drug release strategy, where B-GQDs of the hybrid nanoparticle were triggered by an applied high-frequency magnetic field to generate an induced eddy current whose energy facilitating disassembly of the hybrid nanoparticle of hundred-nanometer size (primary carrier) into constituent units of about 2-5 nm (secondary carrier, such as single dendrimers or single B-GQDs). These constituent units loaded with drugs diffuse more easily from the periphery to interior of a tumor, leading to uniform therapeutic effect on tumors. Furthermore, the hybrid nanoparticle of the present invention can be induced to disassemble even if it reaches deep seated tumors such as brain tumors, because the high-frequency magnetic field penetrates deep into the body.

The present invention is further described in the following examples, in reference to the accompanying drawings. It should be understood that the examples given below do not limit the scope of the invention, and that modifications can be made without departing from the scope of the appended claims.

DETAILED DESCRIPTION OF THE PREFERRED EMBODIMENT

Figure 1:
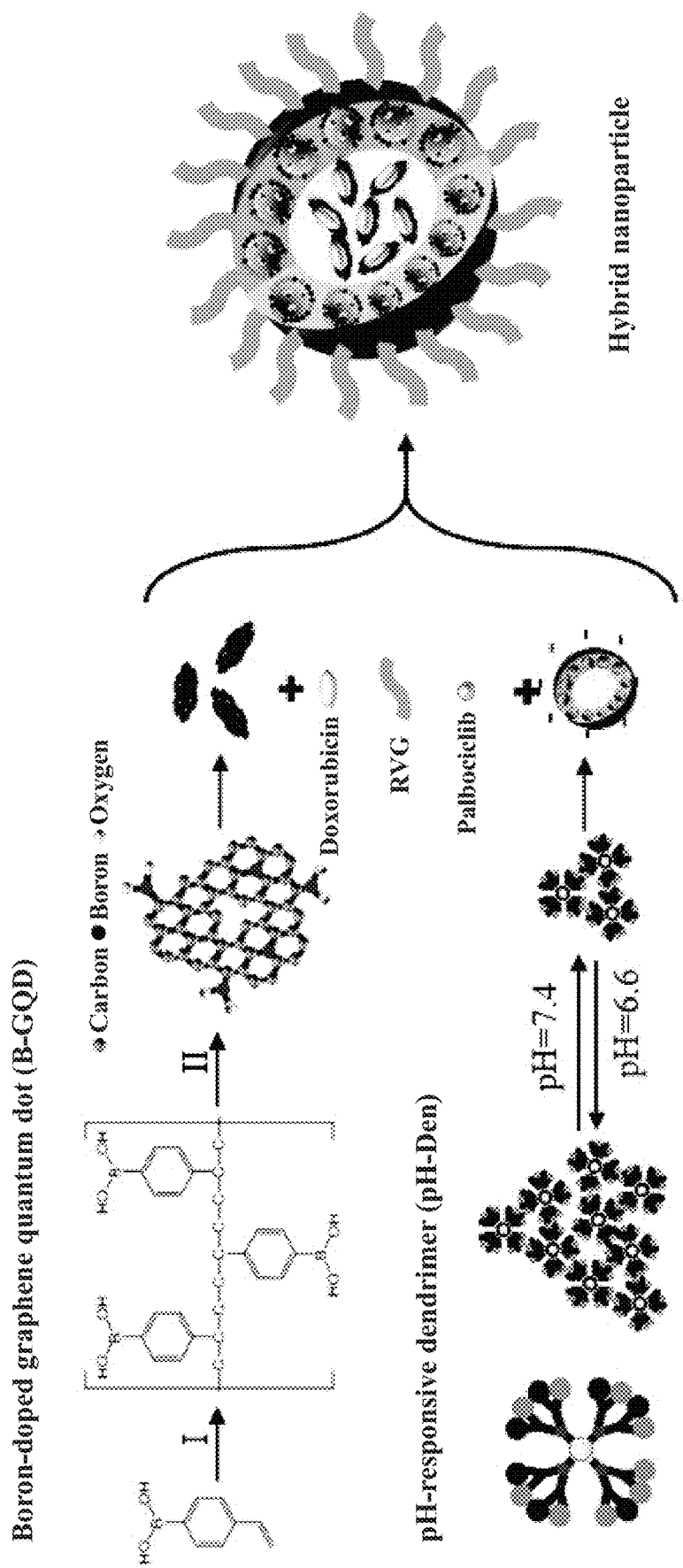
FIG. 1 shows the self-assembly process and structure of a hybrid nanoparticle according to one embodiment of the present invention, in which an aggregate is assembled from the molecules of palbociclib-bound pH-responsive dendrimers (pH-Den), the doxorubicin-bound boron-doped graphene quantum dots (B-GQDs) are localized in the aggregate, and the rabies virus glycoprotein fragments (RVG) adsorb to the surface of the aggregate through electrostatic forces.

The present invention provides a hybrid nanoparticle, including an aggregate assembled from a plurality of polymeric molecules, and a plurality of boron-doped graphene quantum dots (B-GQDs) localized in the aggregate. Each of the polymeric molecules and B-GQDs may carry different drugs. The present invention also provides a method of controlling disassembly of a hybrid nanoparticle, including the steps of obtaining the aforementioned hybrid nanoparticle, and applying a high-frequency magnetic field of 50 to 600 kHz to the hybrid nanoparticle to induce disassembly thereof. The following examples demonstrate the preparation methods of B-GQDs and self-assembly of the hybrid nanoparticle, which includes pH-responsive dendrimers as an exemplary polymeric molecule in one embodiment. The hybrid nanoparticle has been shown to have high stability in aqueous solutions, low drug leakage, and the ability to expand in size with decreasing environmental pH of tumors. Also, the hybrid nanoparticle is induced by the high-frequency magnetic field to disassemble into constituent units, leading to a large amount of drug-loaded constituent units penetrating the dense extracellular matrix and distributing uniformly throughout the tumors. Furthermore, when the hybrid nanoparticle is modified with a rabies virus glycoprotein fragment to form a rabies virus-like particle, the hybrid nanoparticle is able to penetrate the blood-brain barrier and enhance the accumulation of loaded drug in the brain tumor.

In view of the characteristics mentioned above, the hybrid nanoparticle of the present invention is suitable for use in the preparation of tumor-penetrating drug carriers. When drug-loaded hybrid nanoparticles with a diameter of about 200 nm are administered to cancer patients for treatment, it is speculated that that they would circulate in the blood stream and then penetrate across slits of vascular walls in tumor (at a size of about a hundred to several hundred nanometers) and specifically accumulate in the tumor due to the enhanced permeability and retention (EPR) effect. In response to the slightly acidic environment of the tumor (pH 6.5-7.0), the hybrid nanoparticles containing the pH-responsive polymeric molecules expand to a diameter of about 450 nm and thus readily retain in the tumor, resulting in increased accumulation of the loaded-drug in the tumor. Thereafter, when exposed to the high-frequency magnetic field, the hybrid nanoparticles are induced to disassemble into constituent units of about 2-5 nm, thereby the loaded drugs are delivered to the whole tumor by said constituent units with better penetration, resulting in expanded distribution of drugs in the tumor and improved therapeutic effects.

Definition

Numerical quantities provided herein are approximated, experimental values that may vary within 20 percent, preferably within 10 percent, and most preferably within 5 percent. Thus, the terms "about" and "approximately" refer to within 20 percent, preferably within 10 percent, and most preferably within 5 percent of a given value or range.

The term "polymeric molecule" used herein refers to a macromolecule formed by polymerization of one or multiple types of molecules, such as dendrimers, polyethylene glycols, polysaccharides (i.e., hyaluronic acid), and lipids (i.e., phospholipids). The polymeric molecule can be chemically modified to become stimuli-responsive, and its molecular weight preferably ranges from 1,000 to 60,000 Da. The polymeric molecules can self-assemble into structurally stable particles in water or aqueous solutions.

Materials and Methods
Materials 4-vinylphenylboronic acid, boric acid, 4-(bromomethyl) phenylboronic acid, doxorubicin hydrochloride (a water-soluble salt of doxorubicin), ethanol, acetone, dimethyl sulfoxide (DMSO), and generation 2 (G2) polyamidoamine (PAMAM) dendrimer were purchased from Sigma-Aldrich (St. Louis, Mo., USA). Palbociclib hydrochloride (a water soluble salt of palbociclib) was purchased from MedChemExpress (Monmouth Junction, N.J., USA). Fluorescent dyes including cyanine 5.5 (Cy5.5) and rhodamine B isothiocyanate (RITC) were purchased from Molecular Probes (Eugene, Oreg., USA).

Transmission Electron Microscopy (TEM)

TEM images of hybrid nanoparticles and components thereof were obtained using transmission electron microscope JEOL JEM-2010 (200 kV, Tokyo, Japan). The TEM samples were prepared by dropping 5 μl of a freshly prepared aqueous solution (2 mg/ml) of the sample onto a copper grid coated with polyvinyl formal resin (Formvar). After 30-second deposition, excess droplet was blotted away with filter paper. These steps were repeated 3 times, and then the TEM samples were dried overnight at room temperature.

Cell Culture

A mouse astrocytoma cell line ALTS1C1 (ATCC CRL-2541) was purchased from American Type Culture Collection (ATCC). The cells were cultured at 37° C. under 5% $CO_2$ in DMEM medium (Gibco Dulbecco's modified Eagle's medium; Thermo Fisher Scientific) supplemented with 10% fetal bovine serum (FBS; Biological Industries, Cromwell, Conn., USA) and 1% penicillin and streptomycin (Gibco, Thermo Fisher Scientific).

Animal Study

C57BL/6 mice were inoculated intracranially with 2 μL of ALTS1C1 tumor cells ($5 \times 10^7$ cells/mL) and randomized into groups (6 mice per group). At day 14 after the tumor inoculation, 100 μL of a solution of the indicated hybrid nanoparticles (1 mg/mL) was administered intravenously through the tail vein. The hybrid nanoparticles were dissolved in phosphate buffered saline (PBS; 137 mM sodium chloride, 2.7 mM potassium chloride, 4.3 mM disodium hydrogen phosphate, 1.4 mM potassium dihydrogen phosphate, dissolved in deionized water, pH 7.4).

Statistical Analysis

Statistically significant difference among experimental data was determined by Student's t test.

Example 1

Preparation of Boron-Doped Graphene Quantum Dots (B-GQDs)

This example exemplifies the method of preparing one essential constituent molecule of the hybrid nanoparticle of the present invention, that is, the boron-doped graphene quantum dot (B-GQD). 75 mg of 4-vinylphenylboronic acid and 150 mg of boric acid were dissolved in a mixed solution of 2.5 mL of ethanol and 15 mL of acetone. After the solution was ultra-sonicated for 0.5 to 1 hour, 2.5 mL of 30% hydrogen peroxide was slowly added. The resulting mixed solution was ultra-sonicated for 10 minutes and heated at 150 to 400° C. for 2 to 48 hours to obtain a B-GQD crude product. The crude product was cooled and transferred into a dialysis membrane with a molecular weight cutoff of 1000 Da (OrDial D-Clean Dialysis Membranes MWCO:1000; Orange Scientific) in order for dialysis against deionized water at room temperature for three days, during which the water was changed once a day. Thereafter, B-GQD attached to the dialysis membrane were collected and dried to obtain B-GQD powder, which was stored at −20° C.

Example 2

Preparation of Hybrid Nanoparticles
2.1 Preparation of pH-Responsive Dendrimers

The hybrid nanoparticle of the present invention preferably includes stimuli-responsive polymeric molecules which allow the size of the hybrid nanoparticle to increase in the tumor environment, for example, in the weakly acidic tumor environment (with a pH value of about 6.5-7.0). In the present example, the method of preparing the stimuli-responsive polymeric molecules is exemplified by synthesis of a pH-responsive dendrimer (referred to as pH-Den) having a molecular weight ranging from 1,000 to 60,000 Da. 4.4 mg of 4-(bromomethyl)phenylboronic acid and 100 mg of G2 PAMAM dendrimers were dissolved in DMSO for reaction at 80° C. for 24 hours to obtain a crude product of PAMAM dendrimers modified with phenylboronic acid (PBA-PAMAM), which is an example of the pH-responsive dendrimer. The crude product was cooled and transferred into a dialysis membrane with a molecular weight cutoff of 1000 Da (OrDial D-Clean Dialysis Membranes MWCO:1000; Orange Scientific) in order for dialysis against deionized water at room temperature for three days, during which the water was changed once a day. The dialyzed PBA-PAMAM solution was lyophilized to yield pH-Den powder, which was stored at −20° C.

2.2 Preparation of B-GQD/pH-Den Hybrid Nanoparticles

One embodiment of the hybrid nanoparticle of the present invention can be obtained by mixing the B-GQD described in Example 1 with the pH-Den described in Example 2.1. Prior to the mixing step, each of the two constituent units of the hybrid nanoparticle may be combined with a drug to become drug-loaded. In one example, 1 mg of palbociclib hydrochloride was dissolved in 10 μL of ethanol and diluted with double deionized water to yield a palbociclib solution at 1 mg/mL; and 1 mg of doxorubicin hydrochloride was dissolved in 1 mL of double deionized water to obtain a doxorubicin solution at 1 mg/mL. Thereafter, 1 mg of B-GQD was dissolved in deionized water to reach 1 mg/mL, and then mixed with the doxorubicin solution. The resultant mixture was ultra-sonicated for 30 minutes to obtain a doxorubicin-bound B-GQD solution, wherein doxorubicin was loaded on B-GQD via 7E-7E stacking interaction. Also, 1 mg of pH-Den was dissolved in ethanol to reach 1 mg/mL, and then mixed with the palbociclib solution. The mixture was ultra-sonicated for 30 minutes, vacuum dried, and redissolved in deionized water to obtain a palbociclib-bound pH-Den solution at 1 mg/mL, wherein palbociclib was loaded on the hydrophobic core of pH-Den via hydrophobic interactions. Finally, the doxorubicin-loaded B-GQD solution and the palbociclib-bound pH-Den solution were mixed at a volume ratio ranging from 1:2 to 1:8 and ultra-sonicated for 10 to 30 minutes to yield a solution of B-GQD/pH-Den hybrid nanoparticles.

2.3 Modification with Rabies Virus Glycoprotein Fragments

To improve the ability to target a particular tissue, the hybrid nanoparticle of the present invention may further include a targeting molecule on the surface. The targeting molecule may be nucleic acids, sugars, lipids, proteins, or combination thereof. For instance, surface modification with a rabies virus glycoprotein fragment (RVG; with the amino acid sequence of YTIWMPENPRPGTPCDIFTNSRGKRASNGGGGRRRRRR RRR, SEQ ID NO: 1) increases the ability of the B-GQD/pH-Den hybrid nanoparticles described in Example 2.2 to target the nervous system and to penetrate the blood-brain barrier. In one example, 10 μL of a PBS solution containing 200 μg/mL rabies virus glycoprotein fragments (a synthetic peptide purchased from Sigma-Aldrich) was added to a solution of 1 mg/mL B-GQD/pH-Den hybrid nanoparticle with vortexing for about 30 seconds. This step allows the positively charged rabies virus glycoprotein fragments to adsorb electrostatically to the negatively charged pH-sensitive dendrimers on the surface of the hybrid nanoparticles.

FIG. 1 shows the self-assembly process and structure of the aforementioned hybrid nanoparticle. The hybrid nanoparticle, from inner to outer side, includes a self-assembled aggregate of pH-responsive dendrimers with a B-GQD core and an outermost layer of rabies virus glycoprotein fragments. The two nanomaterials, the B-GQD and pH-Den, establish two environments which enable the hybrid nanoparticle to carry drugs with different chemical structures and properties, such as doxorubicin and palbociclib.

Example 3

Structure and Characteristics of the Hybrid Nanoparticles

Figure 2A:
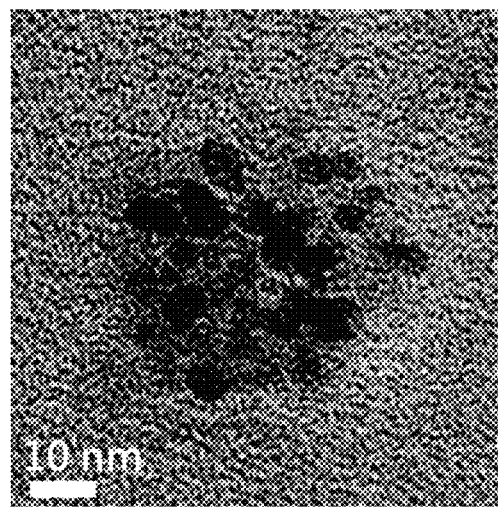
FIG. 2A shows a transmission electron microscopy (TEM) image of boron-doped graphene quantum dots, in which the scale bar represents 10 nm.
Figure 2B:
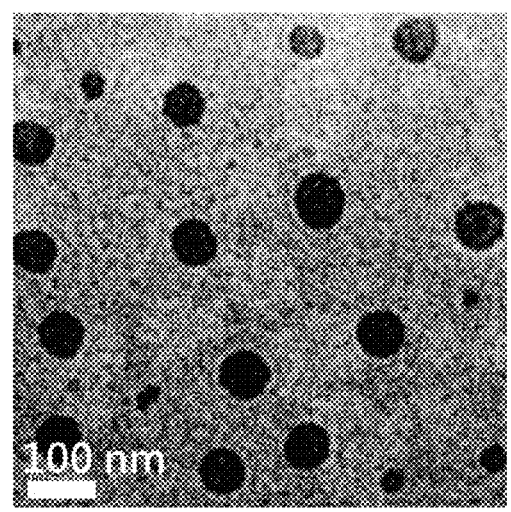
FIG. 2B shows a TEM image of polyamidoamine dendrimers modified with phenylboronic acid, in which the scale bar represents 100 nm.

In order to examine the structure and characteristics of the hybrid nanoparticle of the present invention, transmission electron microscopy (TEM) was used to monitor the morphology and behavior of B-GQD/pH-Den hybrid nanoparticles described in Example 2.2 and the constituent units thereof. FIG. 2A shows a TEM image of boron-doped graphene quantum dots; and FIG. 2B shows a TEM image of polyamidoamine dendrimers modified with phenylboronic acid (an example of the pH-responsive dendrimer). According to FIG. 2A, the boron-doped graphene quantum dots form clusters in water, and each quantum dot has a particle size of about 2 to 5 nm. According to FIG. 2B, the pH-responsive dendrimers self-assemble in water into a sphere having a particle size of about 50 to 80 nm. FIGS. 2A and 2B demonstrate that the boron-doped graphene quantum dots and polyamidoamine dendrimers modified with phenylboronic acid are successfully synthesized.

Figure 3A:
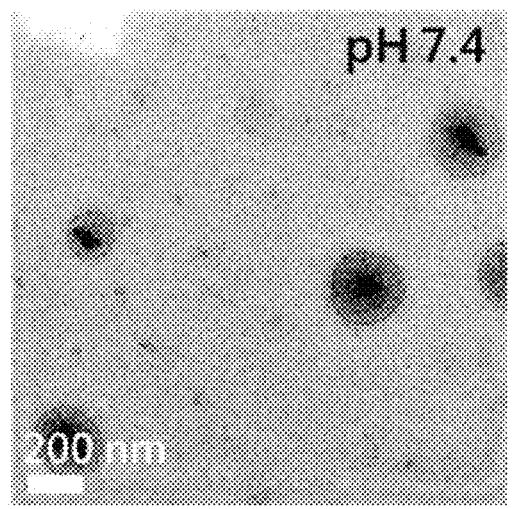
FIG. 3A shows a TEM image of B-GQD/pH-Den hybrid nanoparticles at pH 7.4, in which the scale bar represents 200 nm.
Figure 3B:
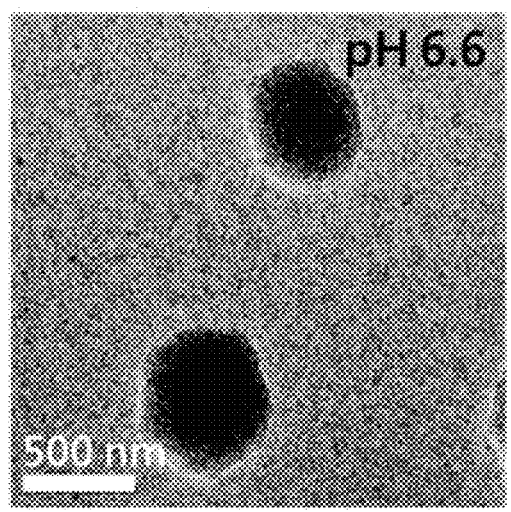
FIG. 3B shows a TEM image of B-GQD/pH-Den hybrid nanoparticles at pH 6.6, in which the scale bar represents 500 nm.
Figure 3C:
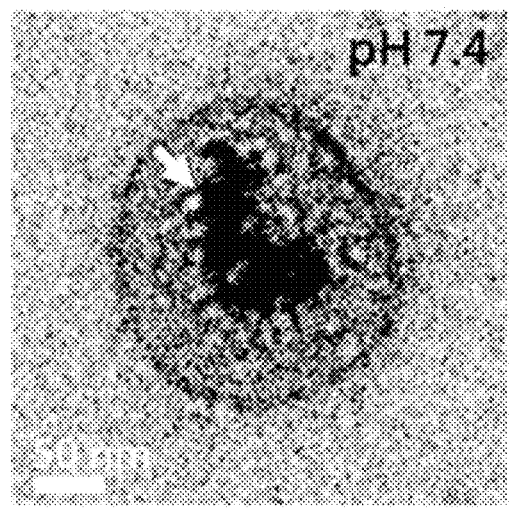
FIG. 3C shows the enlarged view of FIG. 3A, in which the scale bar represents 50 nm, and the white arrow indicates boron-doped graphene quantum dots.
Figure 3D:
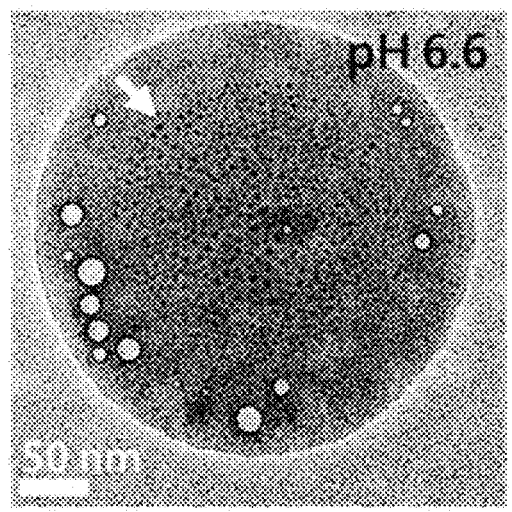
FIG. 3D shows the enlarged view of FIG. 3B, in which the scale bar represents 50 nm, and the white arrow indicates boron-doped graphene quantum dots.

FIGS. 3A and 3B show TEM images of B-GQD/pH-Den hybrid nanoparticles at pH 7.4 and pH 6.6, respectively; FIGS. 3C and 3D show enlarged images of FIGS. 3A and 3B, respectively. According to FIGS. 3A-3B, the hybrid nanoparticles self-assemble in water into a structurally stable and uniform sphere, which has a particle size of about 160 to 250 nm at pH 7.4, but has an increased particle size of about 450 nm at pH 6.6. This property of changing size in response to ambient pH enhances the retention of hybrid nanoparticles in tumor.

Figure 4A:
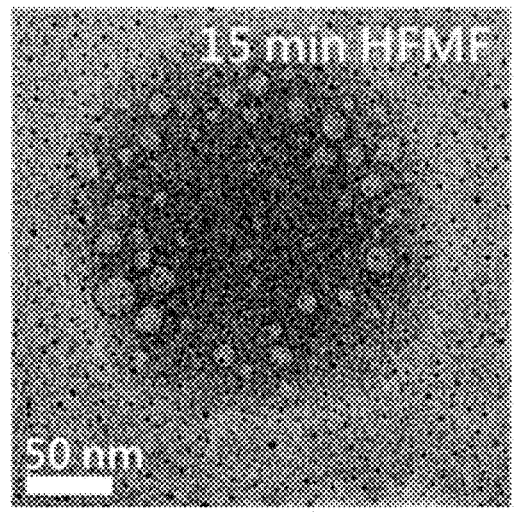
FIG. 4A shows a TEM image of B-GQD/pH-Den hybrid nanoparticles subjected to a high frequency magnetic field (HFMF) for 15 minutes, in which the scale bar represents 50 nm.
Figure 4B:
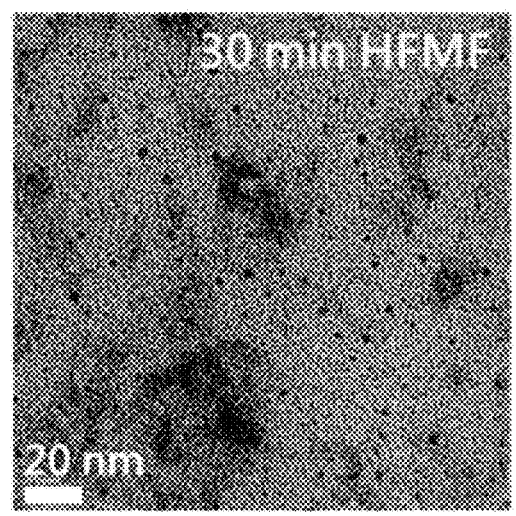
FIG. 4B shows a TEM image of B-GQD/pH-Den hybrid nanoparticles subjected to the high-frequency magnetic field for 30 minutes, in which the scale bar indicates 20 nm.

FIGS. 4A and 4B show TEM images of B-GQD/pH-Den hybrid nanoparticles subjected to a high-frequency magnetic field of 50 to 600 kHz (Power Cube 32/900 high frequency generator; Taiwan Daxian Optics) for 15 minutes and 30 minutes, respectively. These images demonstrate that when the high-frequency magnetic field is applied, the presence of B-GQDs allows the hybrid nanoparticles to fully disassemble into their constituent units with a particle size of about 2 to 5 nm, that is, single boron-doped graphene quantum dots and single pH-responsive dendrimers. Said disassembly is attributed to the energy of an induced eddy current generated on the boron-doped graphene quantum dots that destroys the aggregating interaction between the boron-doped graphene quantum dots and the pH-sensitive dendrimers. This feature facilitates drug release from the hybrid nanoparticles and spread of the drug to all parts of tumors, thereby enhancing the therapeutic effect of drugs on cancerous areas.

Example 4

The Matrix-Penetrating Ability of the Hybrid Nanoparticles after Induced to Disassemble In order to evaluate the ability of each constituent units released from the hybrid nanoparticles of the present invention to penetrate the extracellular matrix when the hybrid nanoparticles are induced to disassemble, confocal laser scanning microscopy (ZEISS LSM 780; Germany) was used to image the three dimensional distribution of hybrid nanoparticles (prepared as 1% aqueous solution and added in an amount of 10 μL) that were added to a solid collagen hydrogel (10 wt %) and then subjected to a high-frequency magnetic field (at frequency of 50 to 600 kHz) for 15 or 30 minutes. The hybrid nanoparticles were assembled from fluorophore-labeled B-GQDs (labeled with RITC, whose NCO group was bonded to the surface depression of quantum dots via covalent bonding) and pH-responsive dendrimers (labeled with Cy5.5, which was embedded in the dendrimers through hydrophobic interactions). RITC was excited at a wavelength of 420 nm and detected at a wavelength of 600 nm. Cy5.5 was excited at 640 nm and detected at 720 nm.

Figure 5A:
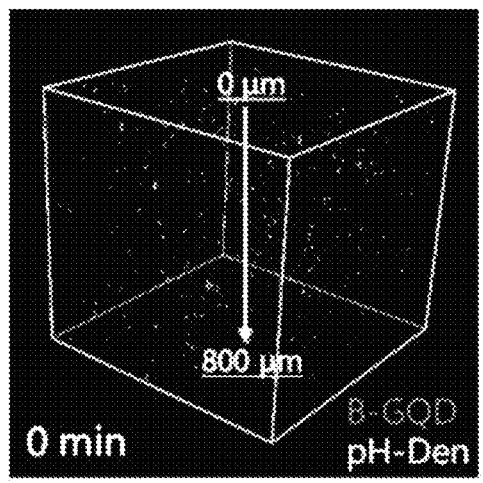
FIG. 5A shows fluorescence signal distribution of the fluorescently labeled B-GQD/pH-Den hybrid nanoparticles in a solid collagen hydrogel before exposure to a high-frequency magnetic field.
Figure 5B:
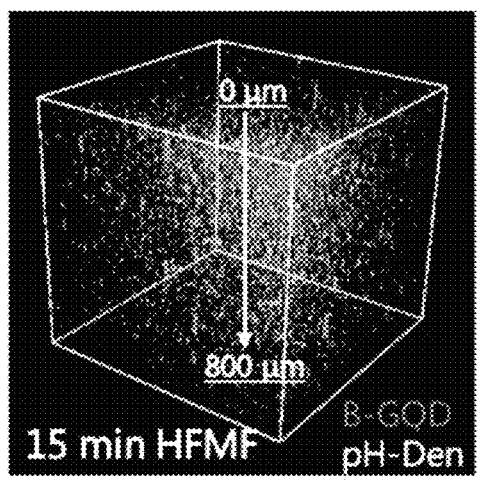
FIG. 5B shows fluorescence signal distribution of the fluorescently labeled B-GQD/pH-Den hybrid nanoparticles in a solid collagen hydrogel after exposure to the high-frequency magnetic field for 15 minutes.
Figure 5C:
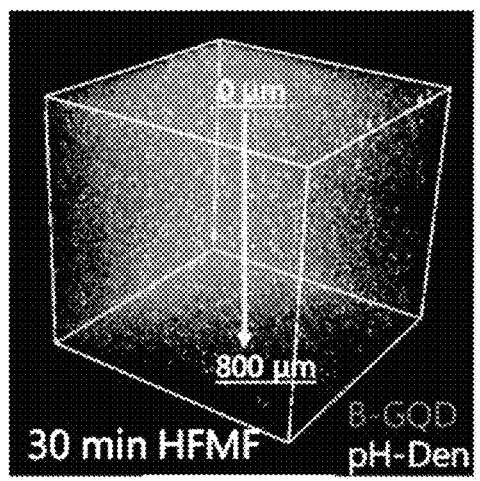
FIG. 5C shows fluorescence signal distribution of the fluorescently labeled B-GQD/pH-Den hybrid nanoparticles in a solid collagen hydrogel after exposure to a high frequency magnetic field for 30 minutes.

FIG. 5A shows the fluorescence signal distribution in a cube (with an edge of about 800 μm) of the collagen hydrogel before the application of high-frequency magnetic field (0 minutes). Compared with FIG. 5A, the fluorescence signals were distributed in a broader region after the exposure to the high-frequency magnetic field for 15 minutes (FIG. 5B) or 30 minutes (FIG. 5C), indicating that the constituent units released from the disassembled hybrid nanoparticles were capable of penetrating the dense collagen hydrogel. This observation of increased penetration is considered to result from the disassembling forces of the hybrid nanoparticles and the ultra-small size of the constituent units. Accordingly, the hybrid nanoparticles of the present invention can be utilized to enhance the penetration of loaded drugs in the dense extracellular matrix.

Example 5

Distribution of the Hybrid Nanoparticles in the Tumor

To examine the distribution of the hybrid nanoparticles of the present invention in the tumor before or after the induced disassembly, confocal laser scanning microscopy (ZEISS LSM 780; Germany) was used to image the fluorescence from the hybrid nanoparticles (prepared as 1% aqueous solution and added in an amount of 50 μL) that were administered for 4 hours to tumor spheroids formed with the mouse astrocytoma cell line ALTS1C1 and then subjected to a high-frequency magnetic field (at frequency of 50 to 600 kHz) for 5 minutes. The hybrid nanoparticles were assembled from fluorophore-labeled B-GQDs (labeled with RITC) and pH-responsive dendrimers (labeled with Cy5.5). The MTSs were formed by injecting $10^6$ ALTST1 cells into a PDMS mold and incubating the cells at 37° C. under 5% $CO_2$ for one day in DMEM medium supplemented with 10% FBS and 1% penicillin and streptomycin. The PDMS mold had a circular reservoir with a diameter of 300 μm and a depth of 300 μm.

Figure 6A:
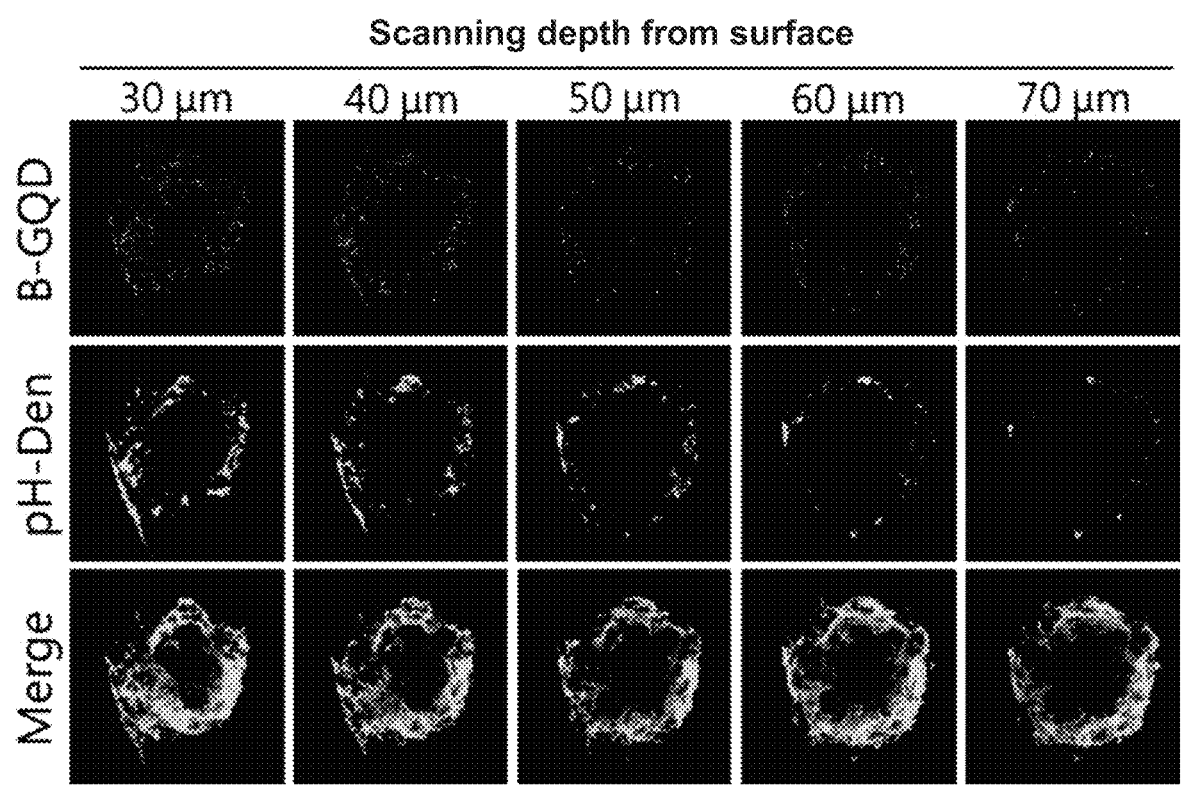
FIG. 6A shows the fluorescence signal distribution of the fluorescently labeled B-GQD/pH-Den hybrid nanoparticles in ALTS1C1 tumor spheroids before exposure to a high-frequency magnetic field.
Figure 6B:
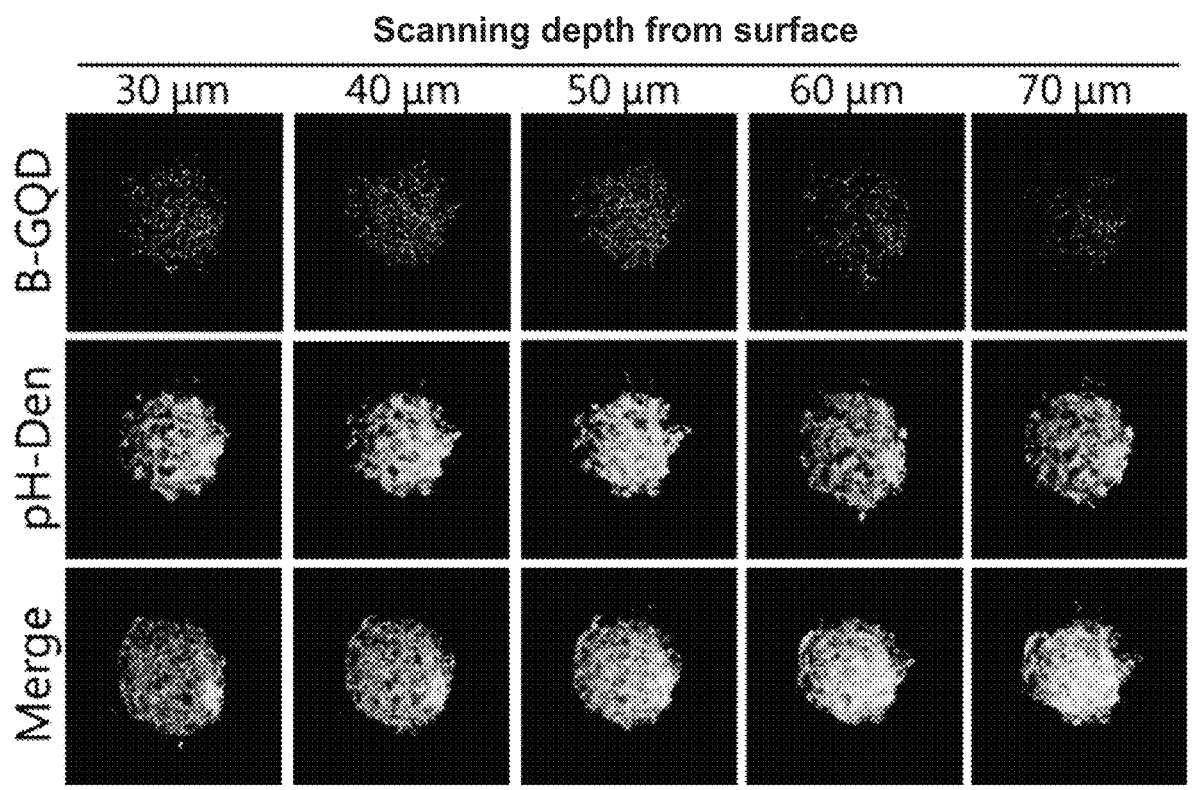
FIG. 6B shows the fluorescence signal distribution of the fluorescently labeled B-GQD/pH-Den hybrid nanoparticles in the ALTS1C1 tumor spheroids after exposure to the high-frequency magnetic field for 5 minutes.

As shown in FIG. 6A, at various tumor depths, the aforementioned hybrid nanoparticles were mainly distributed at the periphery of the tumor spheroid before being subjected to the high-frequency magnetic field. Moreover, the B-GQDs and pH-responsive dendrimers almost overlapped in place, indicating the high stability and low drug leakage of the hybrid nanoparticles. However, as shown in FIG. 6B, when the hybrid nanoparticles were induced to disassemble by the high-frequency magnetic field, the B-GQDs and the pH-responsive dendrimers were uniformly distributed throughout the tumor spheroids, especially located deep in the inner region of the tumor. This result is consistent with the increased penetration of the constituent units observed after the application of high-frequency magnetic field, as disclosed in Example 4. The result also shows that the hybrid nanoparticles of the present invention can improve the therapeutic effect of drugs on cancerous areas.

Example 6

Distribution of the Hybrid Nanoparticles Including Targeting Molecules in the Body To investigate the distribution of the hybrid nanoparticles of the present invention in animal body in the presence or absence of conjugated targeting molecules, 100 μL of a PBS solution containing 1 mg/mL B-GQD/pH-Den hybrid nanoparticles with or without the rabies virus glycoprotein fragment (RVG) was administered via intravenous injection to mice that were inoculated with ALTS1C1 tumor cells in the brain. The distribution and accumulation of the two types of Cy5.5-labeled hybrid nanoparticles in mice were detected 72 hours after the injection by in vivo imaging system (IVIS; PerkinElmer). Cy5.5 was excited at 640 nm and detected at 720 nm. The control mice were only injected with PBS.

Figure 7:
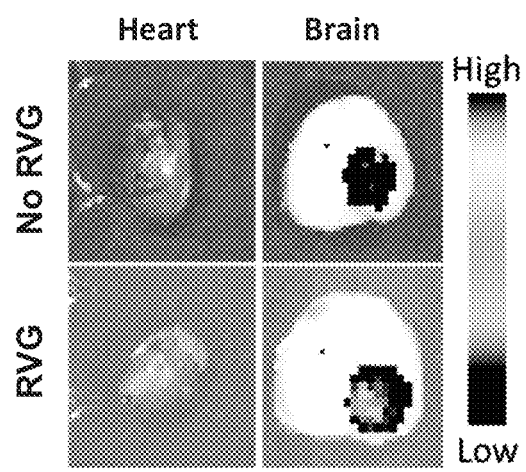
FIG. 7 shows the distribution of B-GQD/pH-Den hybrid nanoparticles with or without the rabies virus glycoprotein fragment (RVG) in the brain and heart of mice; the color bar on the right indicates the color corresponding to high or low fluorescence intensity.
Figure 8:
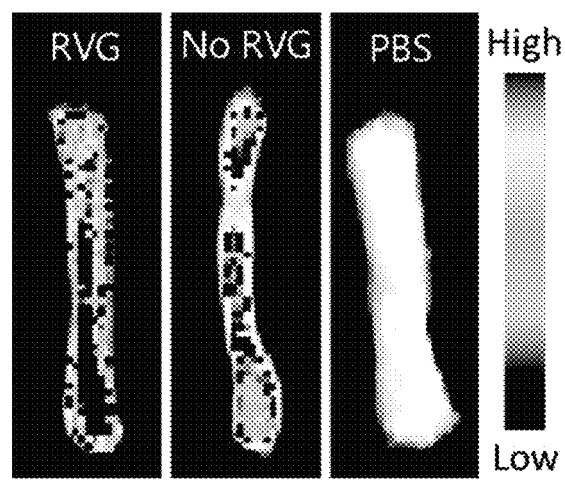
FIG. 8 shows the distribution of B-GQD/pH-Den hybrid nanoparticles with or without the rabies virus glycoprotein fragment (RVG) in the spinal cord of mice; the color bar on the right indicates the color corresponding to high or low fluorescence intensity

As shown in FIG. 7, the cumulative amount of the RVG-modified hybrid nanoparticles in the brain tumor was approximately two-fold higher than that of the hybrid nanoparticles without RVG, indicating that the RVG modification helps the hybrid nanoparticles cross the blood-brain barrier and reduce nanoparticle accumulation in the non-nervous system, thereby reducing the side effects during brain tumor treatment. Furthermore, as shown in FIG. 8, the RVG modification increased the accumulation of the hybrid nanoparticles in the spinal cord, suggesting that the hybrid nanoparticles may accomplish drug delivery to brain tumors by passing through the cerebrospinal fluid in the central nervous system without the need to cross the blood-brain barrier.

In conclusion, the hybrid nanoparticle of the present invention exhibits high stability and low dug leakage in aqueous solution, and can carry different drugs simultaneously. The boron-doped graphene quantum dots included in the hybrid nanoparticle allows the hybrid nanoparticle to disassemble into constituent units under an applied high-frequency magnetic field, thereby making it much easier for the loaded drugs to penetrate the dense extracellular matrix and spread from the periphery to interior of a tumor. Moreover, when the hybrid nanoparticle includes pH-responsive polymeric molecules, both the particle size and retention in the weakly acidic tumor increase, thereby increasing the accumulation of loaded drug in the tumors. While further modified with the rabies virus glycoprotein fragment, the hybrid nanoparticles can penetrate the blood-brain barrier and accumulate more in brain tumors. Accordingly, the hybrid nanoparticle of the present invention may be utilized as a multi-drug delivery platform for penetrating tumors, particularly for treating the deep seated tumors.

Although the present invention has been described with reference to the preferred embodiments, it will be apparent to those skilled in the art that a variety of modifications and changes in form and detail may be made without departing from the scope of the present invention defined by the appended claims.

What is claimed is:

1. A hybrid nanoparticle, comprising:

an aggregate assembled from a plurality of polymeric molecules, and a plurality of boron-doped graphene quantum dots localized in the aggregate;

wherein the polymeric molecule further binds to a hydrophilic drug or a first hydrophobic drug;

wherein the boron-doped graphene quantum dot further binds to a second hydrophobic drug;

wherein the hybrid nanoparticle is configured to be disassembled by applying a high-frequency magnetic field of 50 to 600 kHz;

wherein the hybrid nanoparticle has a particle size of 160-450 nm;

wherein each of the plurality of boron-doped graphene quantum dots has a particle size of 2-5 nm.

2. The hybrid nanoparticle of claim 1, wherein the polymeric molecule is a stimuli-responsive polymeric molecule.

3. The hybrid nanoparticle of claim 2, wherein the stimuli-responsive polymeric molecule is a pH-responsive dendrimer.

4. The hybrid nanoparticle of claim 1, further comprising a targeting molecule.

5. The hybrid nanoparticle of claim 4, wherein the targeting molecule is a rabies virus glycoprotein or a peptide fragment thereof.

6. A method of controlling disassembly of a hybrid nanoparticle, comprising the steps of (a) obtaining the hybrid nanoparticle of claim 1, and (b) applying a high-frequency magnetic field of 50 to 600 kHz to the hybrid nanoparticle to induce disassembly thereof.

7. The method of claim 6, wherein the polymeric molecule is a stimuli-responsive polymeric molecule.

8. The method of claim 7, wherein the stimuli-responsive polymeric molecule is a pH-responsive dendrimer.

9. The method of claim 6, wherein the polymeric molecule further binds to a hydrophilic drug or a hydrophobic drug.

10. The method of claim 6, wherein the boron-doped graphene quantum dot further binds to a hydrophobic drug.

11. The method of claim 9, wherein the boron-doped graphene quantum dot further binds to a hydrophobic drug.

12. The method of claim 6, wherein the hybrid nanoparticle further comprises a targeting molecule.

13. The method of claim 12, wherein the targeting molecule is a rabies virus glycoprotein or a peptide fragment thereof.

* * * * *